US012232898B2

(12) United States Patent
Martinez Ferreira et al.

(10) Patent No.: US 12,232,898 B2
(45) Date of Patent: *Feb. 25, 2025

(54) CABLE MANAGEMENT SYSTEM AND METHOD FOR C-ARM IMAGING SYSTEMS

(71) Applicant: GE Precision Healthcare LLC, Wauwatosa, WI (US)

(72) Inventors: Carlos Martinez Ferreira, Paris (FR); Bernard Bouvier, Éragny (FR); Vincent Parinet, Versailles (FR); Julien Marcotte, Saint Vrain (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 211 days.

This patent is subject to a terminal disclaimer.

(21) Appl. No.: 17/977,155

(22) Filed: Oct. 31, 2022

(65) Prior Publication Data

US 2024/0138789 A1    May 2, 2024

(51) Int. Cl.
*A61B 6/00* (2024.01)

(52) U.S. Cl.
CPC ............ *A61B 6/4441* (2013.01); *A61B 6/44* (2013.01); *A61B 6/4405* (2013.01); *A61B 6/4476* (2013.01); *A61B 6/56* (2013.01)

(58) Field of Classification Search
CPC ........... A61B 6/00; A61B 6/44; A61B 6/4441; A61B 6/56; A61B 6/4405; A61B 6/4476; H02G 11/006
See application file for complete search history.

(56) References Cited

U.S. PATENT DOCUMENTS

| 7,654,738 | B2 | 2/2010 | Fink et al. |
| 9,986,952 | B2 | 6/2018 | Dalvi et al. |
| 10,448,910 | B2 | 10/2019 | Johnson et al. |

(Continued)

FOREIGN PATENT DOCUMENTS

| DE | 19630888 | * | 2/1998 |
| DE | 19630888 A1 | | 2/1998 |
| DE | 202018004739 U1 | | 10/2018 |

(Continued)

OTHER PUBLICATIONS

DE 19630888 Translation of Abstract, Espacenet Search Result Jun. 12, 2024; 1 page.

(Continued)

*Primary Examiner* — Jurie Yun
(74) *Attorney, Agent, or Firm* — Boyle Fredrickson S.C.

(57) ABSTRACT

A C-arm x-ray imaging device includes a base, a carriage operably connected to the base and having at least one axis of movement with respect to the base, a C-arm movably connected to the carriage, the C-arm including a cable management system having a housing disposed on the carriage, the housing defining an interior, a number of cables extending from the base into the interior of the housing, a cable chain having a first end secured within the interior of the housing and a second end affixed to the C-arm, the cable chain defining a channel therein that receives the number of cables to direct the number of cables from the base to the C-arm. The cable management system operate to retain the number of cables in alignment with the C-arm in any orientation of the C-arm relative to the base.

14 Claims, 11 Drawing Sheets

(56) References Cited

U.S. PATENT DOCUMENTS

2019/0029620 A1    1/2019  Baumann et al.
2024/0138802 A1*   5/2024  Martinez Ferreira .... A61B 6/56

FOREIGN PATENT DOCUMENTS

JP    4746270 B2   8/2011
RU    2458629 C2   8/2012

OTHER PUBLICATIONS

DE 202018004739 Translation of Abstract, Espacenet Search Result Jun. 12, 2024; 1 page.
EP application 23202819.1 filed Oct. 10, 2023—Search report issued Mar. 6, 2024; 8 pages.

\* cited by examiner

CABLE MANAGEMENT SYSTEM AND METHOD FOR C-ARM IMAGING SYSTEMS

BACKGROUND OF DISCLOSURE

The subject matter disclosed herein relates to X-ray imaging systems having C-arms and, more particularly, to X-ray imaging systems where the C-arm includes motion along multiple independent rotational axes.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm disposed on a base or gantry. In such cases, the C-arm can often be raised and lowered, be moved from side to side, and/or be rotated about one or more axes of rotation via the moveable arm. Accordingly, such C-arms can be moved and reoriented to allow X-ray images to be taken from several different positions and angles and different portions of a patient, without requiring the patient to be frequently repositioned.

However, rotation or motion of the C-arm may be limited in certain directions (e.g., orbital direction) due to the structure of the imaging system. In particular, the C-am includes a number of cables/cabling connected between the base and the C-arm for supplying power, control signals and data to and from the X-ray source and detector. In these devices, the cables extend outwardly from the base and are connected to the exterior of the C-arm and must each have a length sufficient to accommodate all degrees and ranges of motion of the C-arm in relation to the base, while also being formed in a suitable manner to perform the specified functions, e.g., stiff cables for high voltage power transmission or directing flows of a cooling fluid.

The number, length and stiffness of the cables necessary for the operation of the C-arm and X-ray source and detector disposed thereon can create obstructions to visibility and/or access in areas around the C-arm and the base during movement of the due to the cabling looping into these areas based on the position of the C-arm relative to the base. Further, with regard to the fast movement of the C-arm between different imaging orientations, the cables can become separated from the structure of the C-arm to create an obstruction, particularly in situations where the C-ram is an extended position relative to the gantry or base.

Therefore, it is desirable to develop a cable management system and method for positioning the cables for the C-ram in a manner that maintains the cables in a desired position relative to the C-arm to minimize obstructions in the area around the C-arm and maximize the area available for use by medical practitioners and/or other medical devices for patient treatment.

BRIEF DESCRIPTION OF THE DISCLOSURE

According to one exemplary non-limiting aspect of the disclosure, a C-arm x-ray imaging device includes a base, a carriage operably connected to the base and having at least one axis of movement with respect to the base; a C-arm movably connected to the carriage, the C-arm including an x-ray source and an x-ray detector disposed thereon in alignment with one another and a cable management system having a housing disposed on the carriage, the housing defining an interior, a number of cables extending from the base into the interior of the housing, a cable chain having a first end secured within the interior of the housing and a second end affixed to the C-arm, the cable chain defining a channel therein that receives the number of cables to direct the number of cables from the base to the C-arm.

According to still another aspect of one exemplary non-limiting embodiment of the disclosure, a cable management system for a C-arm X-ray imaging device includes a housing adapted to be secured on a rotating component of a base for the imaging device, the housing defining an interior, a number of cables adapted to be connected between the base for the imaging system and a C-arm and a cable chain having a first end secured within the interior of the housing and a second end adapted to be secured to the C-arm, the cable chain defining a channel therein that receives the number of cables to direct the number of cables from the base to the C-arm, wherein the cable management system is configured to retain the number of cables in alignment with the C-arm in any orientation of the C-arm relative to the base.

According to still another aspect of one exemplary non-limiting embodiment of the disclosure, a method of managing the position of cables connecting a detector and an x-ray source of a C-arm to a base of a C-arm x-ray imaging device including the steps of providing a C-arm-ray imaging device including a base, a carriage operably connected to the base and having at least one axis of movement with respect to the base, a C-arm movably connected to the carriage, the C-arm including an x-ray source and an x-ray detector disposed thereon in alignment with one another and a cable management system having a housing disposed on the carriage, the housing defining an interior, a number of cables extending from the base into the interior of the housing, a cable chain having a first end secured within the interior of the housing and a second end affixed to the C-arm, the cable chain defining a channel therein that receives the number of cables to direct the number of cables from the base to the C-arm, placing the number of cables within the cable chain, moving the C-arm relative to the carriage and maintaining the cable chain within a profile of at least one of the housing or the C-arm.

It should be understood that the brief description above is provided to introduce in simplified form a selection of concepts that are further described in the detailed description.

BRIEF DESCRIPTION OF THE DRAWINGS

The drawings illustrate the best mode presently contemplated of carrying out the disclosure. In the drawings.

DETAILED DESCRIPTION

Figure 1:
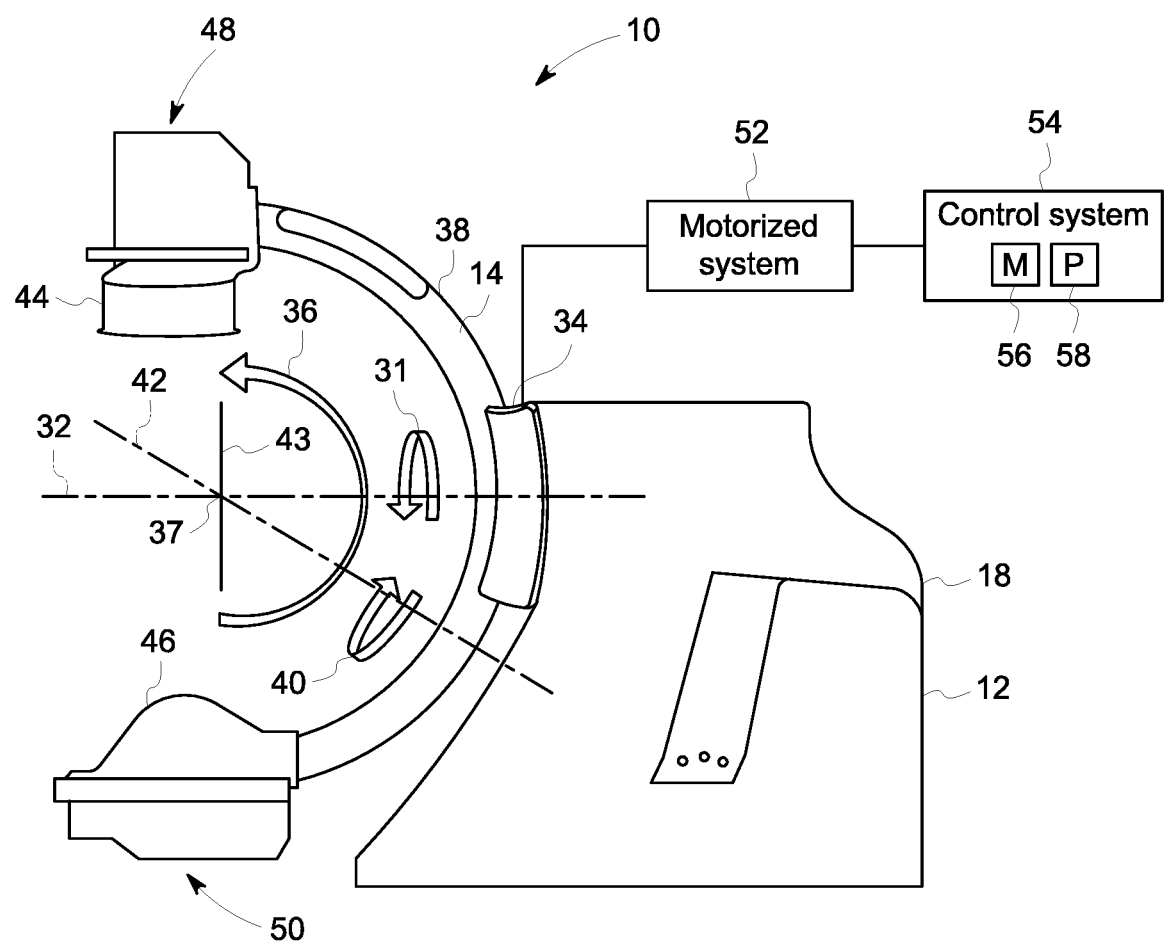
FIG. 1 is a side elevation view of an embodiment of a C-arm imaging system having multiple independent rotational axes.
Figure 2:
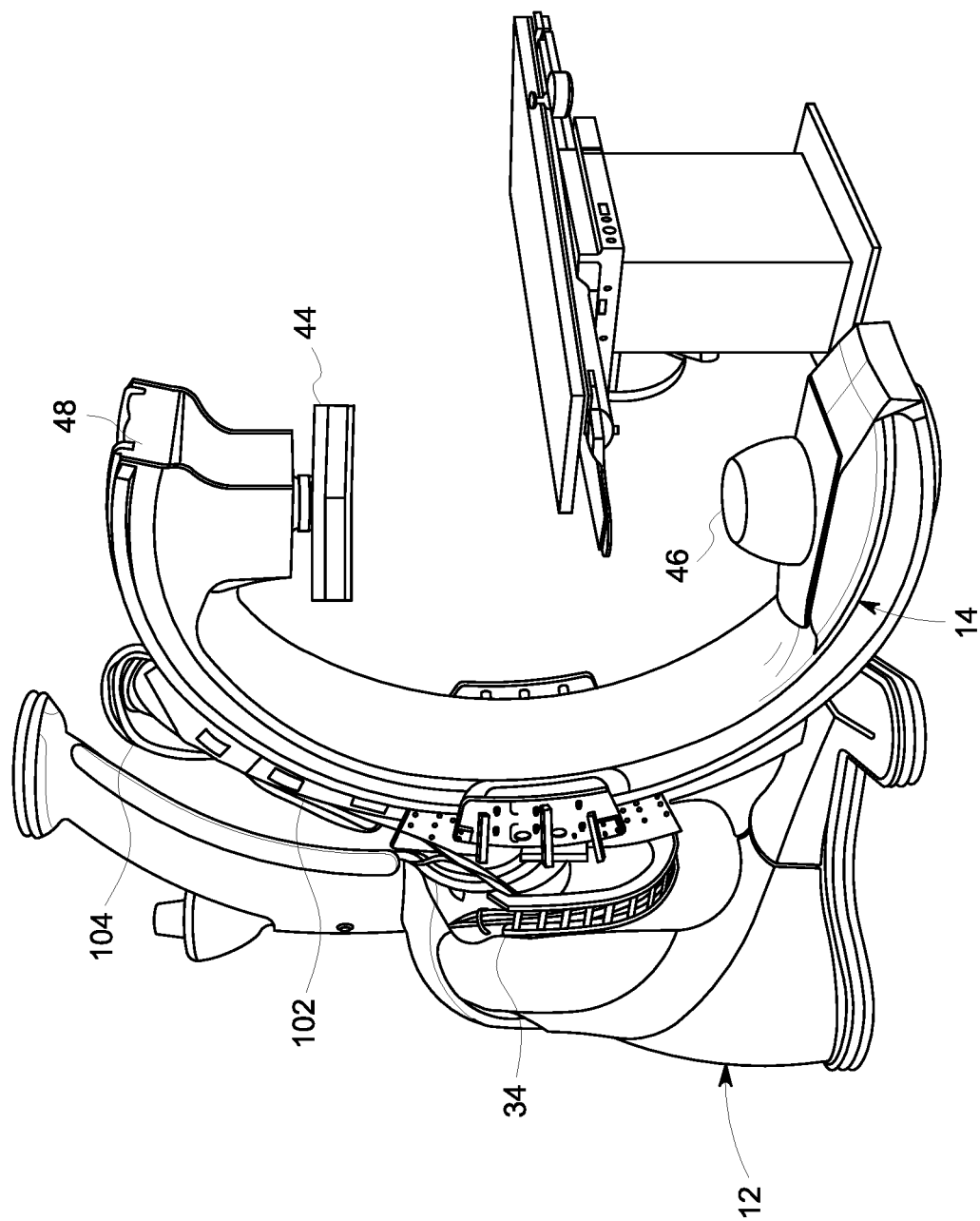
FIG. 2 is an isometric view of an embodiment of the C-arm imaging system of FIG. 1 having multiple independent rotational axes according to one exemplary non-limiting embodiment of the invention.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., fixed X-ray imaging system) having automated C-arm motion about multiple independent (e.g., separate or different) rotational axes (e.g., 3 or more). For example, the C-arm may rotate about 3 different axes: a lateral axis, an orbital axis, and a flip-flop axis (e.g., defined by rotation about where the C-arm is coupled to an L-arm). The motion about these 3 different axes may be automated (e.g., via a motorized system including multiple motors or servomotors). The automated motion about these 3 different axes may increase the orbital range or coverage with the C-arm without having to move the patient and/or table the patient is disposed on. Motorization of all of these axes (especially the flip-flop axis) provides numerous advantages. For example, motorized motion compared to manual motion may be controlled remotely to reduce radiation exposure. In addition, motorization of all these axes enables the capture of image data for three-dimensional (3D) image generation, while still allowing the X-ray imaging system to be utilized as a general purpose C-arm imaging system. However by automating all of these axes, a general purpose C-arm imaging system may also be utilized as an accurate 3D image capturing imaging system.

FIG. 1 is a side view of an embodiment of an X-ray imaging system 10 (e.g., a fixed C-arm imaging system) having multiple independent rotational axes. Although a mobile imaging system is illustrated, the embodiments described below may be utilized with any X-ray imaging system having a C-arm (e.g., a mobile C-arm imaging system). The X-ray imaging system 10 may utilize multiple imaging modalities (e.g., fluoroscopy, computed tomography, tomosynthesis, radiographic, magnetic resonance imaging, etc.) to acquire two-dimensional 2D and/or 3D image data. The X-ray imaging system 10 may be utilized for both diagnostic and interventional imaging. In addition, the X-ray imaging system 10 may be utilized for general purposes (e.g., general radiology, orthopedics, etc.) and special purposes (e.g., image guided surgery).

A principal function of the mobile X-ray imaging system 10 is to generate X-rays for diagnostic and interventional imaging. The X-ray imaging system 10 includes a support structure or base 12, a C-arm 14 connected to the base or gantry 12 via a carriage 34, and a control panel 18. The base 12 provides support for the C-arm 14 and holds the C-arm 14 in a suspended position. The base 12 includes a vertical lift column (not shown) operably connected to the carriage 34 that permits the C-arm 14 and carriage 34 to move vertically in relation to base 12. Vertical lift column can optionally include a horizontal extension arm (not shown) operably connected to the carriage 34 and the vertical lift column that permits the C-arm 14 to move perpendicularly in relation to vertical lift column by movement (e.g., horizontal movement) of the horizontal extension arm in relation to the base 12. The C-arm 14 may be moved along the axis of the horizontal extension arm to effect transverse tracking motion. The carriage 34 is optionally coupled to the horizontal extension arm/base 12 and configured to pivot or rotate about the horizontal extension arm such that the C-arm 14 can be made to pivot in a 360 degree arc in a lateral direction 31 (e.g., circumferential direction) about a lateral axis 32 (e.g., parallel to the horizontal extension arm) relative to the base 12.

The C-arm 14 is coupled to a C-arm rotation device 34 (e.g., carriage) that is coupled to the base 12. The C-arm rotation device/carriage 34 is coupled to an assembly of rollers or wheels (e.g., disposed within a track 38 of the C-arm 14) that enables the C-arm 14 to be directed, move or rotate about an orbital axis 37 (e.g., extending into and out of the page where axes 32, 42 intersect) in an orbital direction 36 along the track 38 relative to C-arm rotation device 34. As described in greater detail below, the X-ray imaging system 10 is configured to enable the C-arm 14 to rotate in the orbital direction 36 to provide an orbital range relative to a location where the C-arm 14 is coupled to the base 12 (i.e., the C-arm rotation device 34).

The C-arm rotation device 34 also enables the C-arm 14 to rotate (e.g., circumferentially) or flip-flop (e.g., as indicated by reference numeral 40) about a flip-flop axis 42 (e.g., flip-flop axis) emanating from where the C-arm rotation device 34 is coupled to the C-arm 14 and, thus, the base 12. The C-arm rotation device 34 enables rotation of the C-arm 14 relative to the C-arm rotation device 34.

Rotation of the C-arm 14 180 degrees (thereby enabling rotation about the lateral axis 32 and the flip-flop axis 42) enables the image chain to rotate 180 degrees about the orbital axis 37. An orbital plane 43 extends perpendicular to the orbital axis 37 and includes the image chain and the C-arm 14. The beginning orientation and the final orientation of the orbital plane 43 remains the same when the C-arm 14 is rotated about the lateral axis 32. However, during movement of the C-arm 14, the orbital plane 43 changes with the largest angular changer occurring when the C-arm 14 is rotated 90 degrees.

An image receptor 44 (e.g., X-ray detector) and an X-ray source 46 are coupled to opposing ends 48, 50 of the C-arm 14 to form an image chain. The C-arm 14 allows the image receptor 44 and the X-ray source 46 to be mounted and positioned about an object to be imaged, such as a patient. The C-arm 14 may be a circular C-shaped or an arc-shaped member, for example. The C-arm 14 enables selective positioning of the image receptor/detector 44 and the X-ray source 46 with respect to the width and length of the patient or other object located within the interior free space of the C-arm 14. The image receptor/detector 44 may be an image intensifier or other energy receptor for using in diagnostic imaging, for example. The image receptor/detector 44 and the X-ray source 46 are used to generate a diagnostic image representative of the object being imaged.

Rotation about the axes 32, 37, and 42 are independent (e.g., separate or different from each other). Rotation of the C-arm 14 with respect to these axes 32, 37, 42 is driven by a motorized system 52. The motorized system 52 may include one or more motors or servomotors to drive the rotation about these axes 32, 37, 42 via automation. The motors or servomotors may be disposed throughout different components of the X-ray imaging system 10 (e.g., the upper housing of base 12, the C-arm rotation device 34, the C-arm 14, etc.). The motorized system 52 may be coupled to control system or controller 54 (e.g., disposed within the base 12 and/or remote from the X-ray imaging system 10). The control system 54 may include a memory 56 and one or more processors 58 to execute code or instructions stored within the memory 56. The control system 52 may control the automated movement of the C-arm 14 about the axes 32, 37, 42.

The automated or motorized movement of the C-arm 14 about the independent axes 32, 37, 42 increases the orbital range or coverage about the orbital axis 37 (i.e., allows the C-arm 14 to be rotated in the orbital direction 36). In particular, the orbital range may be increased to 180 degrees or greater. In particular, orbital rotation of the C-arm 14 180 degrees is achieved by rotating the C-arm 14 180 degrees about the lateral axis 32 and 180 degrees about the flip-flop axis 42.

Looking now at FIGS. 2, 4, 5 and 9-12, the imaging system 10 can include a cable management system 100 formed in part of a housing 102 disposed on and extending outwardly from one or both sides of the carriage 34. In the illustrated exemplary embodiment, the housing 102 is formed with a shape 102 that conforms to the shape of the C-arm 14 when a portion of the C-arm 14 is disposed adjacent the housing 102. A number of cables 104 extending from the base 12 and/or carriage 34 are positioned along an exterior 106 of the housing 102 opposite the C-arm 14 and around an end 108 of the housing 102 opposite the base 12/carriage 34 into an interior 110 of the housing 102. The cables 104 are secured to the exterior 106 of the housing 102 in any suitable manner (e.g., by mechanical fasteners) in order to maintain the position of the cables 104 relative to the housing 102 and carriage 34 when the carriage 34 and enclosure 34 are rotated with respect to the base 12 during the operation of the imaging system 10.

Figure 11:
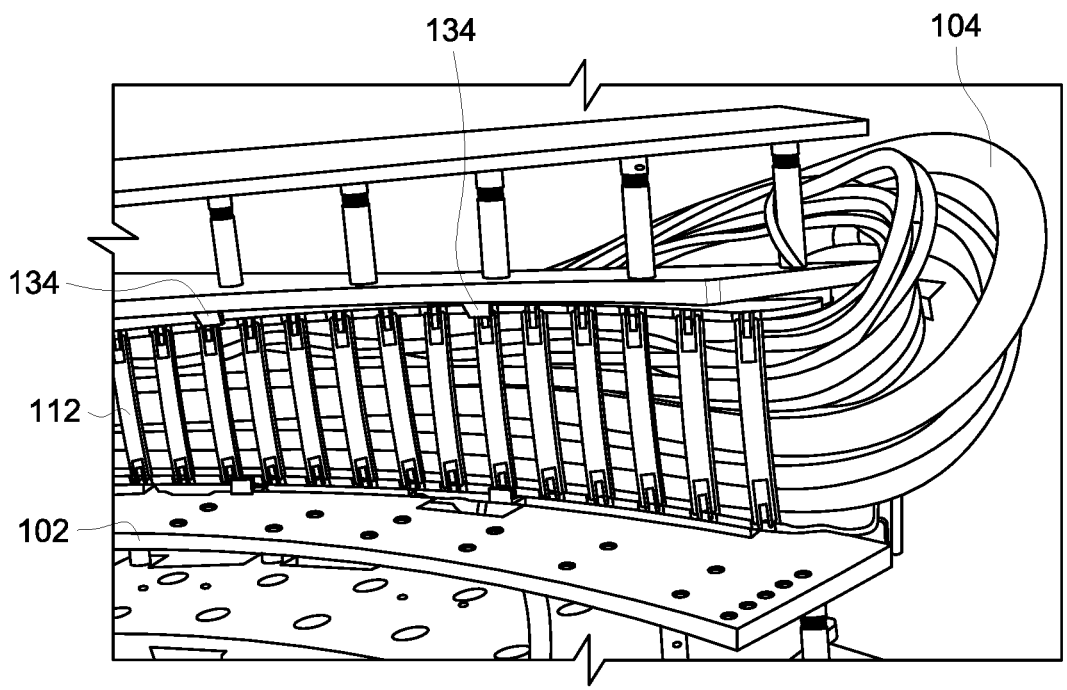
FIG. 11 is a partially broken away isometric view of the cable chain of FIG. 10 engaged with engagement members disposed within the cable housing of the C-arm imaging system of FIG. 9 according to an exemplary embodiment of the disclosure.

As best shown in FIG. 11, within the interior 110 of the housing 102, the cables 104 are positioned within a cable chain 112 in order to maintain the order and alignment of the cables 104 with regard to the C-arm 14 during operation of the imaging system 10. The cable chain 112 is formed of a number of interconnected, articulating sections 114 that each define a channel 116 therein to receive the cables 104. The sections 114 each have a pair of side walls 118,120 pivotally joined to side walls 118,120 of adjacent sections 114, and pair of enclosure walls 122,124 extending between the side walls 118,120 to define the channel 116 therein. The pivoting connection of the sections 114 to one another allows the cable chain 112 to curve and maintain the alignment of the cable chain 112 with the C-arm 14.

One end 126 of the cable chain 112 is affixed to the housing 102 within the interior 110 adjacent the end 108. In this position the cables 104 can be directly inserted within the cable chain 112 in any suitable manner and routed through the cable chain 112. Opposite the end 108 of the housing 102, the other, second end 129 of the cable chain 112 is connected to the C-arm 14 at a location/connection point 128, e.g., adjacent the detector 44, where the cables 104 can be routed along and/or within the C-arm 14 for direct or other operable connection to the detector 44 and/or to the X-ray source 46.

Figure 3:
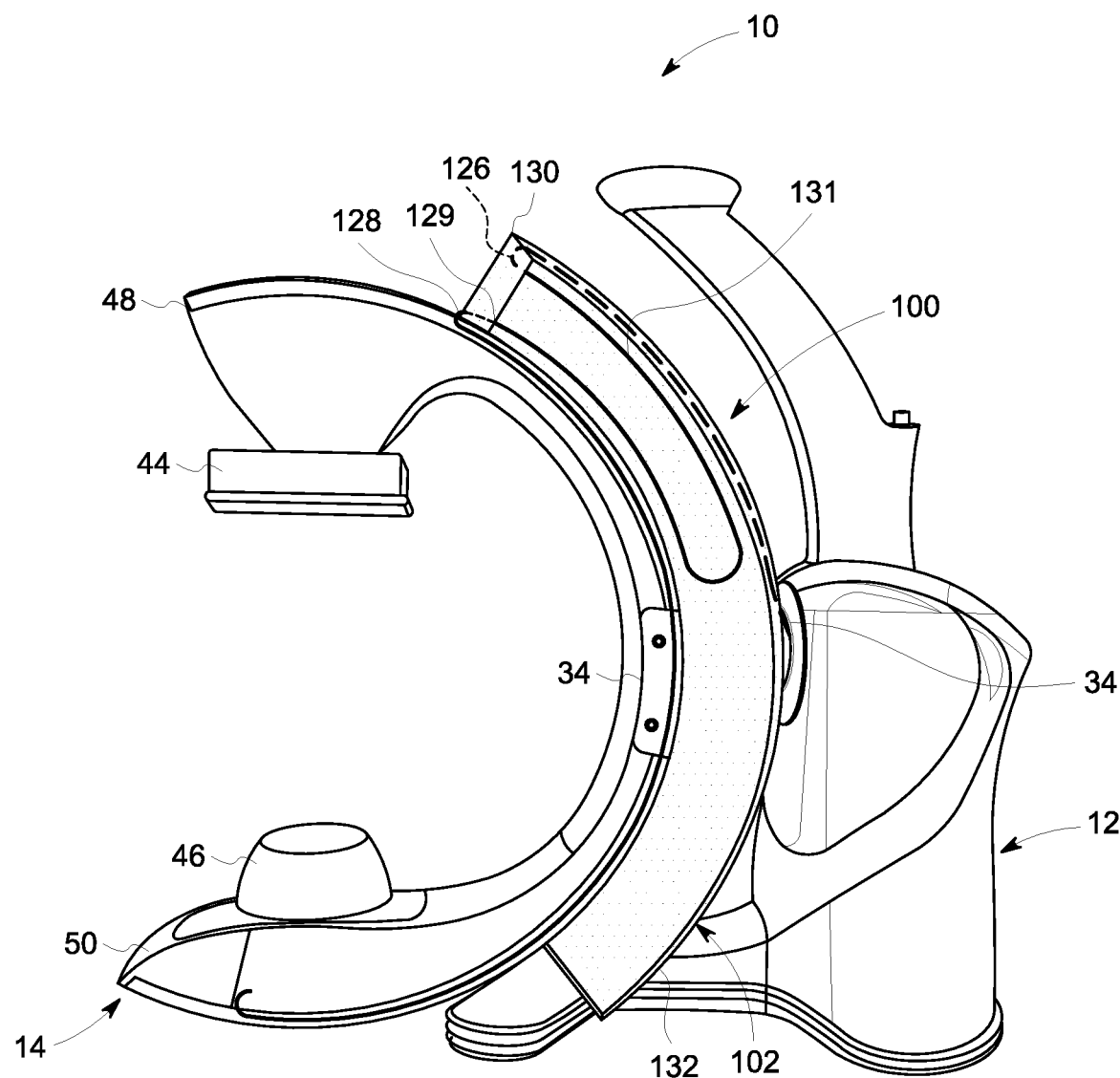
FIG. 3 is a partially broken away, side elevational view of the C-arm imaging system of FIG. 2 with the detector a vertical position.
Figure 4:
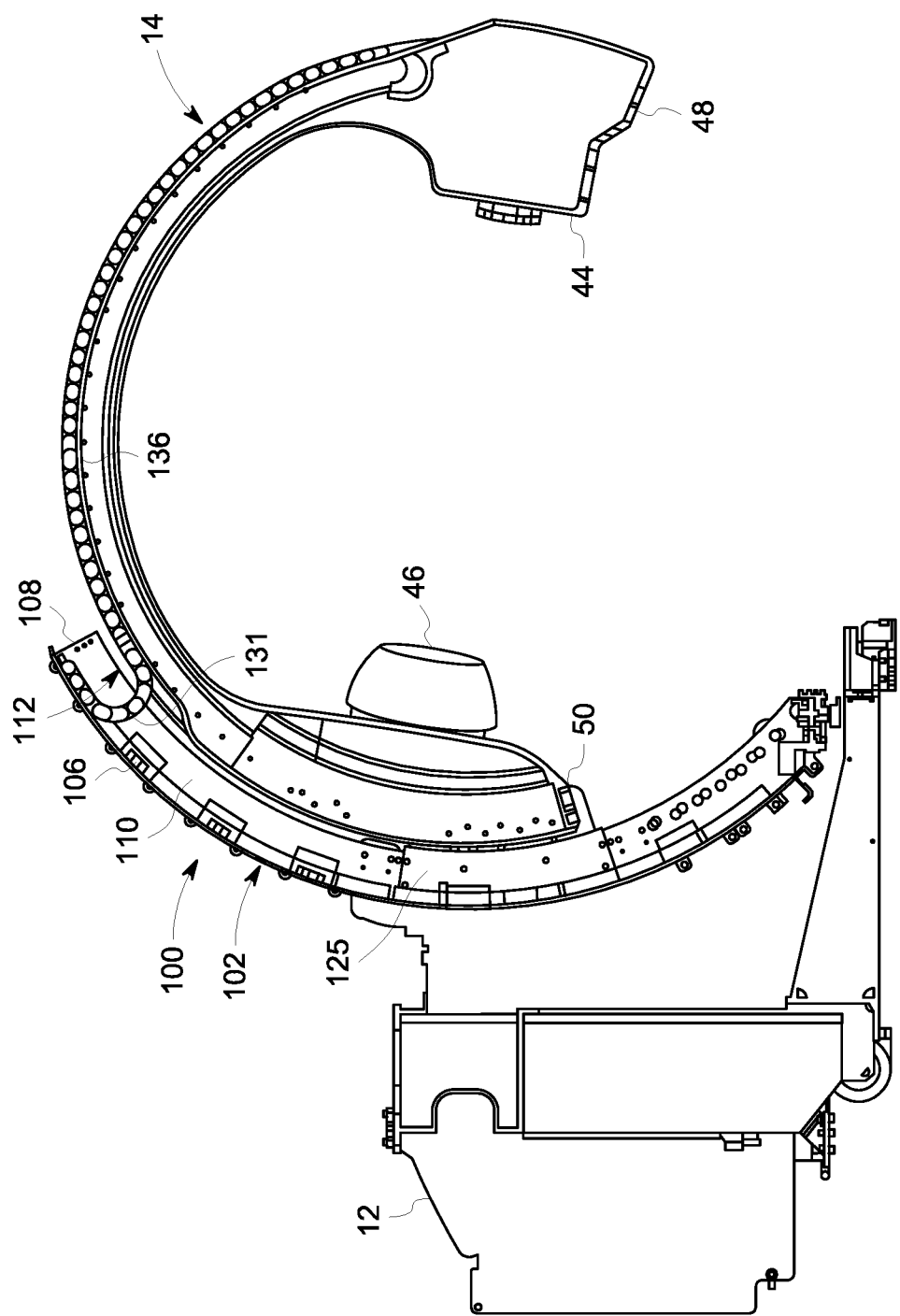
FIG. 4 is a partially broken away, side elevational view of the C-arm imaging system of FIG. 2 with the detector rotated +105 degrees relative to the position of FIG. 3.
Figure 5:
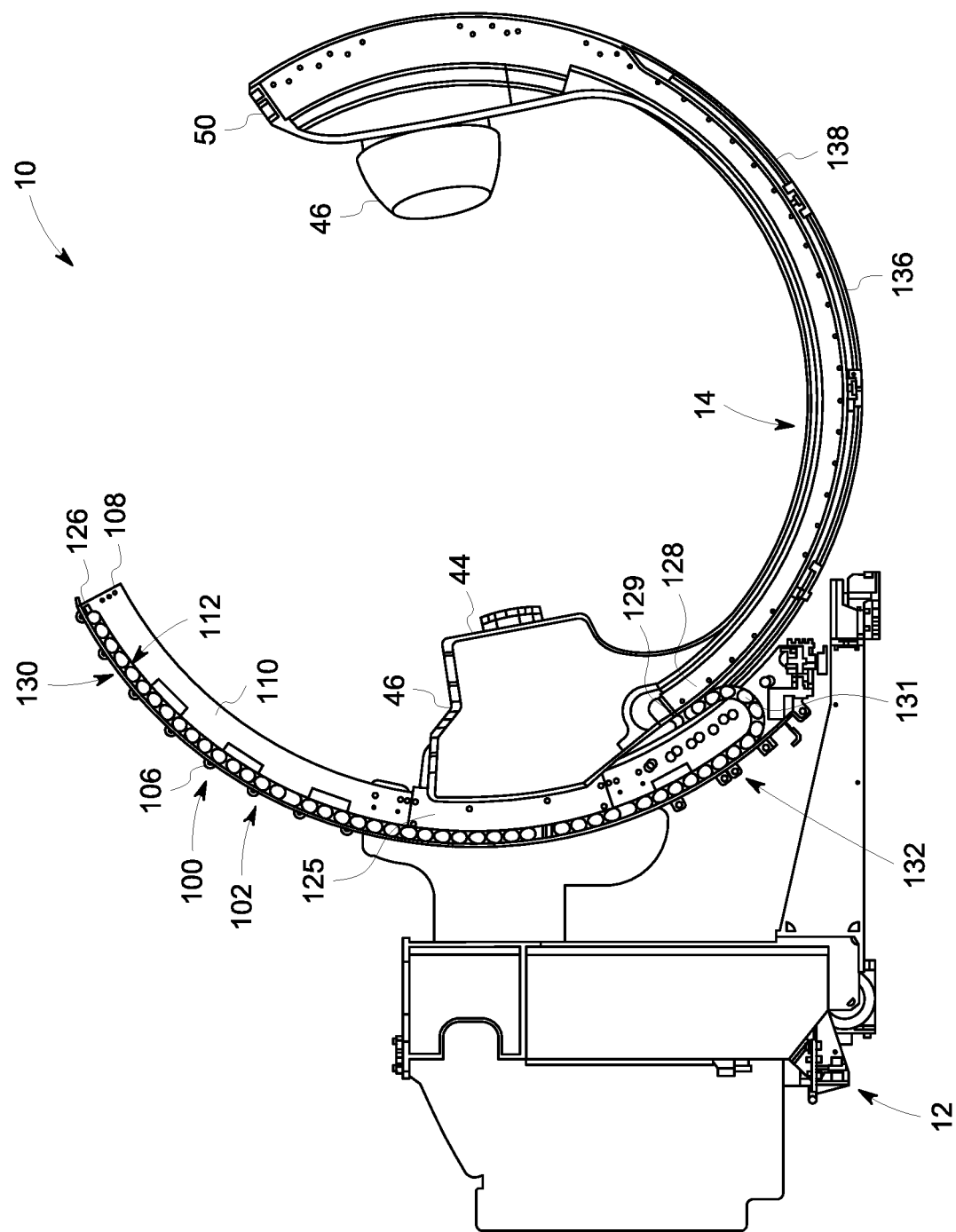
FIG. 5 is a partially broken away, side elevational view of the C-arm imaging system of FIG. 2 with the detector rotated −105 degrees relative to the position of FIG. 3.

With regard now to FIGS. 3-5, in one exemplary embodiment, the housing 102 is formed to extend from each side of the carriage 34 along the shape of the C-arm 14, defining an upper housing 130 and a lower housing 132. In a vertical position for the C-arm imaging system 10 (FIG. 3), the cable chain 112 is oriented within the interior 110 of the housing 102 in an inverted loop 131, with the cable chain 112 initially extending from the end 108 of the housing 102 towards the carriage 34. Adjacent the carriage 34, the cable chain 112 then curves, i.e., curves in an inward and upward direction towards the C-arm 14, and reverses direction to extend along the housing 102 adjacent the C-arm 14 to the connection of the cable chain 112 to the C-arm 14, such that the entire length of the cable chain 112 is retained within the upper housing 130. As the carriage 34 and the C-arm 14 define a space 125 therebetween to allow for free movement of the C-arm 14 relative to the carriage 34, the space 125 allows for the disposition and movement of the cable chain 112 between the C-arm 14 and the carriage 34 without impairing movement of the C-arm 14 with regard to the carriage 34.

In FIG. 4, when the C-arm 14 is moved from the vertical position of FIG. 3 to a horizontal position at one end of the range of motion of the C-arm 14 where the detector 44 is disposed opposite the base 12 and/or carriage 34, the connection point 128 is disposed away from the base 12. As the C-arm 14 moves to this position, the second end 129 of the cable chain 112 secured to the connection point 128 moves along with the C-arm 14 to draw the cable chain 112 out of the upper housing 130. The articulation provided to the cable chain 112 by the pivoting engagement of the sections 114 forming the cable chain 112 allows the cable chain 112 to closely conform to the C-arm 14, and thus not present any obstructions in the area surrounding the C-arm 14.

Looking now at FIG. 5, when the C-arm 14 is moved to the other end of the range of motion of the C-arm 14, i.e., with the X-ray source 46 positioned generally opposite the base 12, the cable chain 12 remains connected to the end 108 of the housing 102. However, in this position of the C-arm 14, the cable chain 112 extends along the interior 110 of both the upper housing 130 and the lower housing 132 within the space 125 between the C-arm 14 and the carriage 34. In this position of the C-arm 14, the cable chain 112 is entirely disposed within the housing 102, such that there are no obstructions formed by the cable chain 112 to interfere with a physician or other equipment positioned and/or moving around the C-arm 14.

Figure 9:
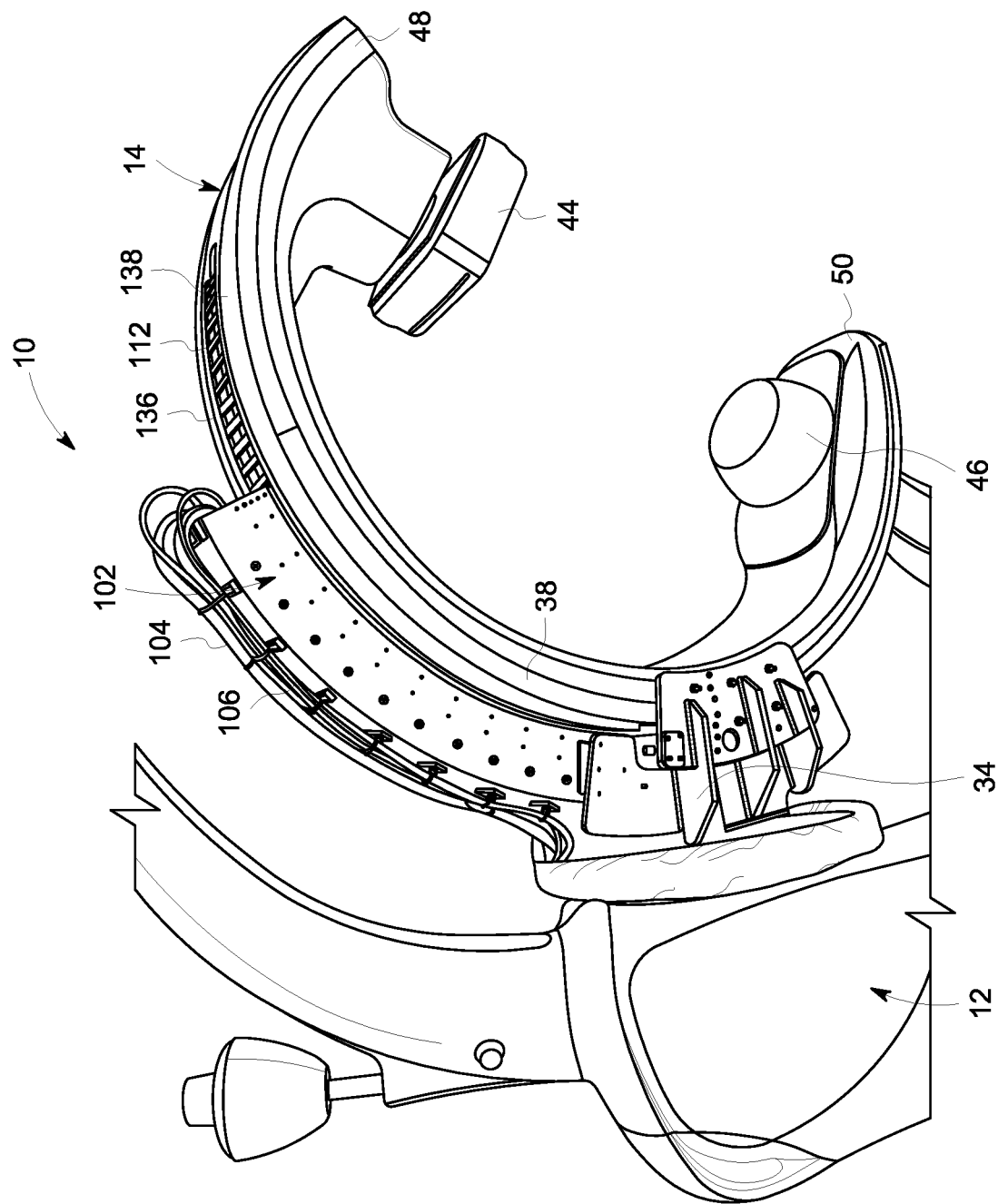
FIG. 9 is an isometric side view of the C-arm imaging system of FIG. 2 according to another exemplary embodiment of the disclosure.
Figure 12:
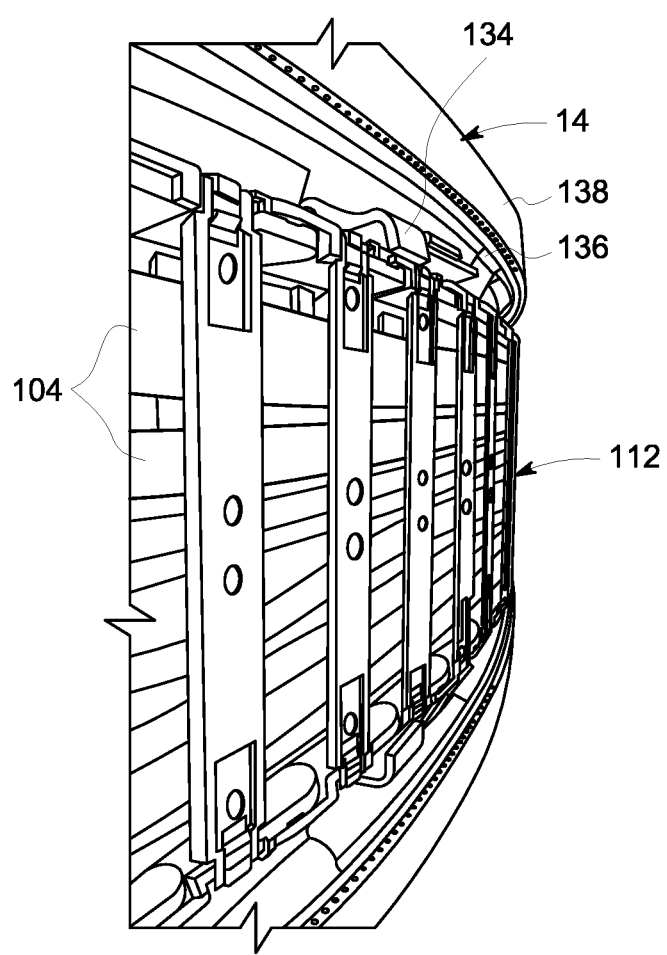
FIG. 12 is a perspective view of the cable chain of FIG. 10 engaged with a clamping mechanism disposed within the channel of the C-arm according to an exemplary embodiment of the disclosure.

Additionally, according to another exemplary embodiment illustrated in FIGS. 9, 11 and 12, which can be employed alone or in conjunction with other embodiments, to assist in holding the cable chain 112 in the desired configuration within the housing 102, the housing 102, e.g., the upper housing 130 and/or the lower housing 132, can include a number of engagement mechanisms 134 disposed in the interior 110 of the housing 102. The engagement members 134 can take any suitable form, such as any one or more of a magnetic holding member, a cam operated holding member, or a flexible or spring biased holding member or pusher, among others. The engagement members 134 operate to selectively engage and hold the cable chain 112 within the housing 102,130,132 until the movement of the C-arm 14, and consequent movement of the cable chain 112 disengages the cable chain 112 from the engagement structures 134. Conversely, any movement of the C-arm 14 that repositions the cable chain 112 within the housing 102,130, 132 causes the engagement members 134 to re-engage the cable chain 112 to hold the cable chain 112 in the interior 110 of the housing 102,130,132. With the engagement members 134, the movement of the cable chain 112 corresponding to the movement of the C-arm 14 can effectively be directed along the space 125 to prevent interference of the cable chain 112 with movement of the C-arm 14, in addition to preventing obstructions of the cable chain 112 in the area surrounding the C-arm 14.

Figure 10:
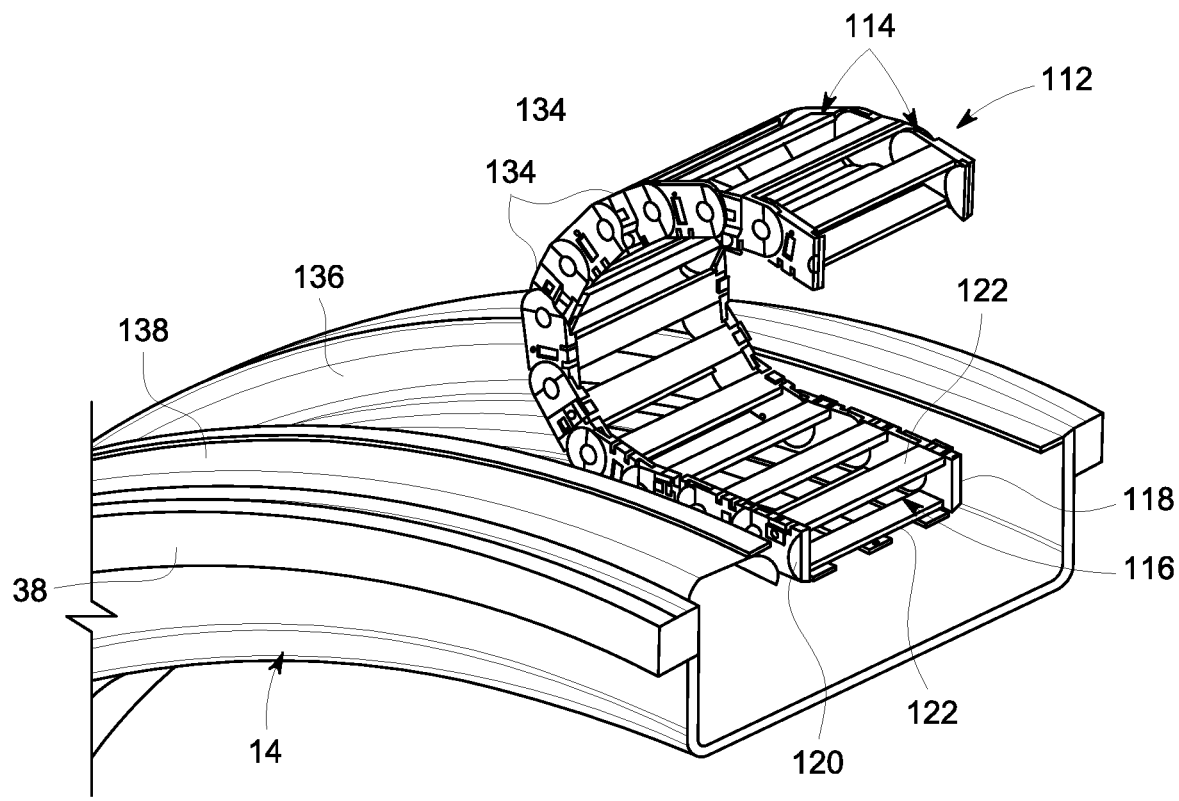
FIG. 10 is a partially broken away isometric view of a cable chain releasably engaged within a channel in the C-arm of the C-arm imaging system of FIG. 9.

In still another exemplary embodiment of the disclosure illustrated in FIGS. 9, 10 and 12, which can be employed along with other embodiments, to assist in positioning the cable chain 112 in a non-obstructing position when the C-arm 14 is in the position of FIG. 4, the C-arm 14 can include a groove 136 formed in an outer surface 138 of the C-arm 14. The groove 136 is shaped to receive the portions of the cable chain 112 therein when the cable chain 112 is disposed against the outer surface 138 of the C-arm 14, such as shown in FIG. 4. When disposed within the groove 136, the cable chain 112 is retained within the profile of the C-arm 14 such that no part of the cable chain 112 extends outwardly from the C-arm 14 to present any obstruction to physicians and/or equipment in the area surrounding the C-arm 14. Further, the cable chain 112 can be retained within the groove 136 by gravity and/or by the operation of a number of engagement members 134 as described previously that disposed within the groove 136 and operable to engage and disengage the cable chain 112 in correspondence with the movement of the C-arm 14.

Figure 6:
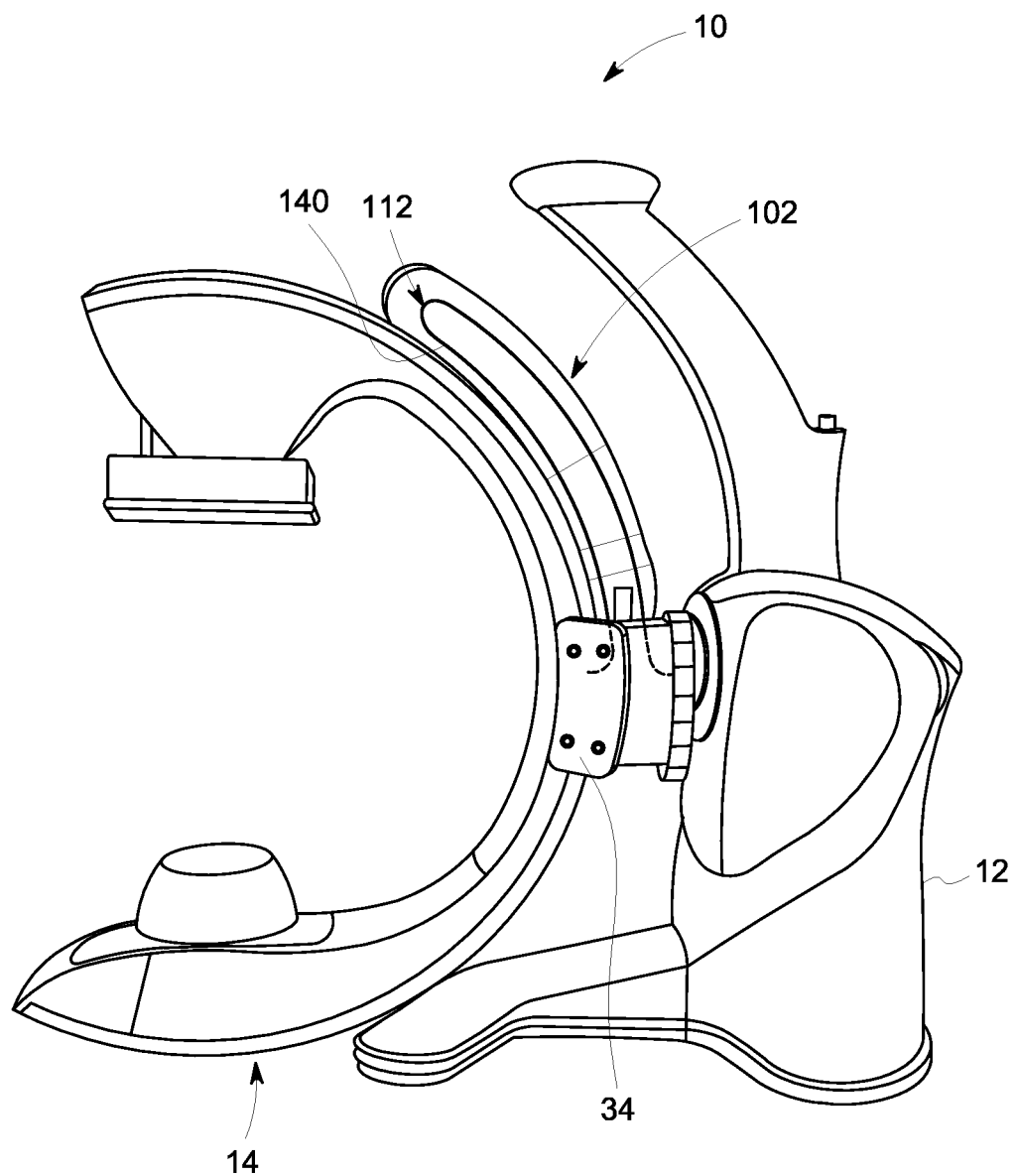
FIG. 6 is a partially broken away, side elevational view of a C-arm imaging system according to another exemplary embodiment of the disclosure with the detector a vertical position.
Figure 7:
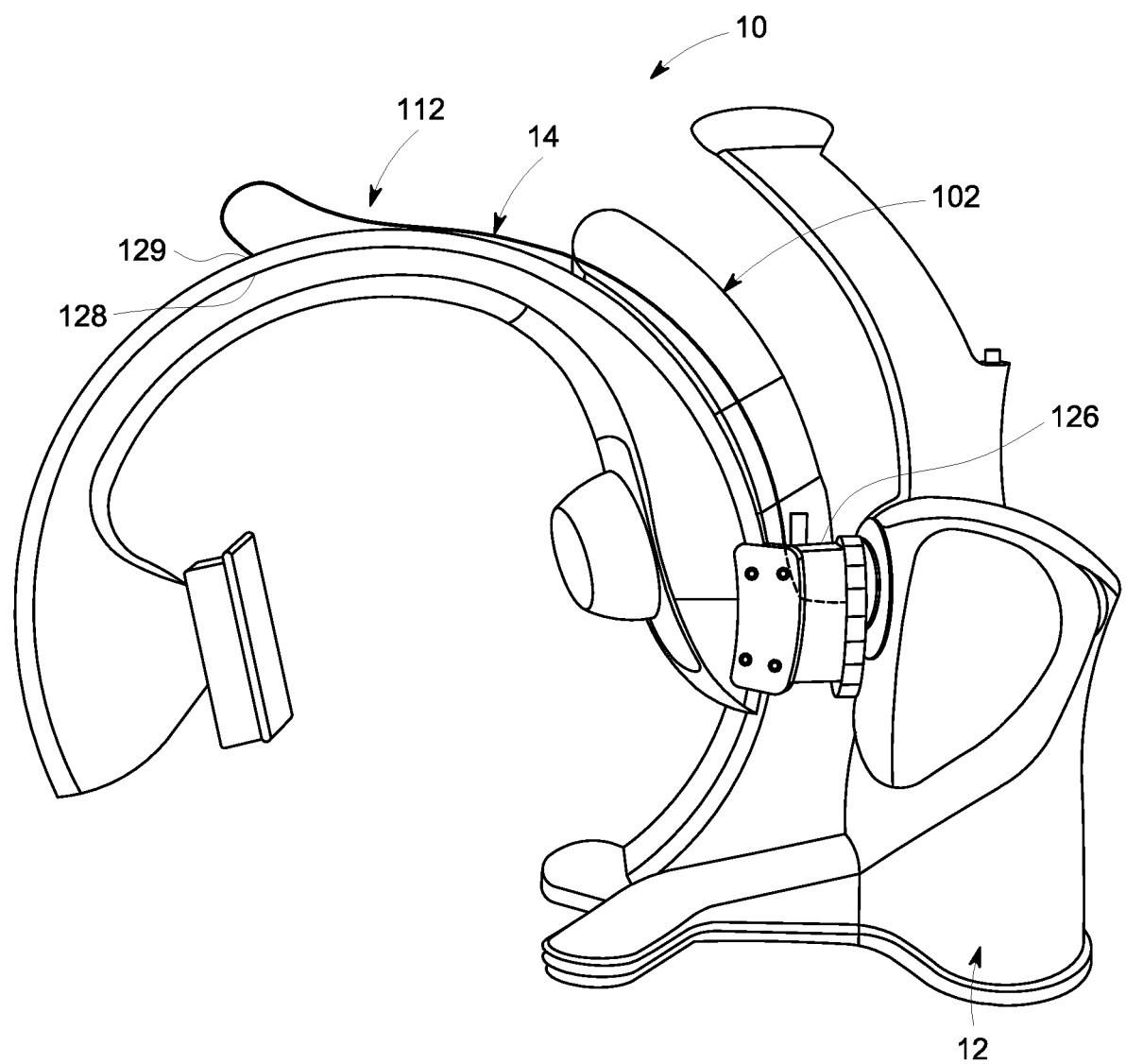
FIG. 7 is a partially broken away, side elevational view of the C-arm imaging system of FIG. 6 with the detector rotated +105 degrees relative to the position of FIG. 6.
Figure 8:
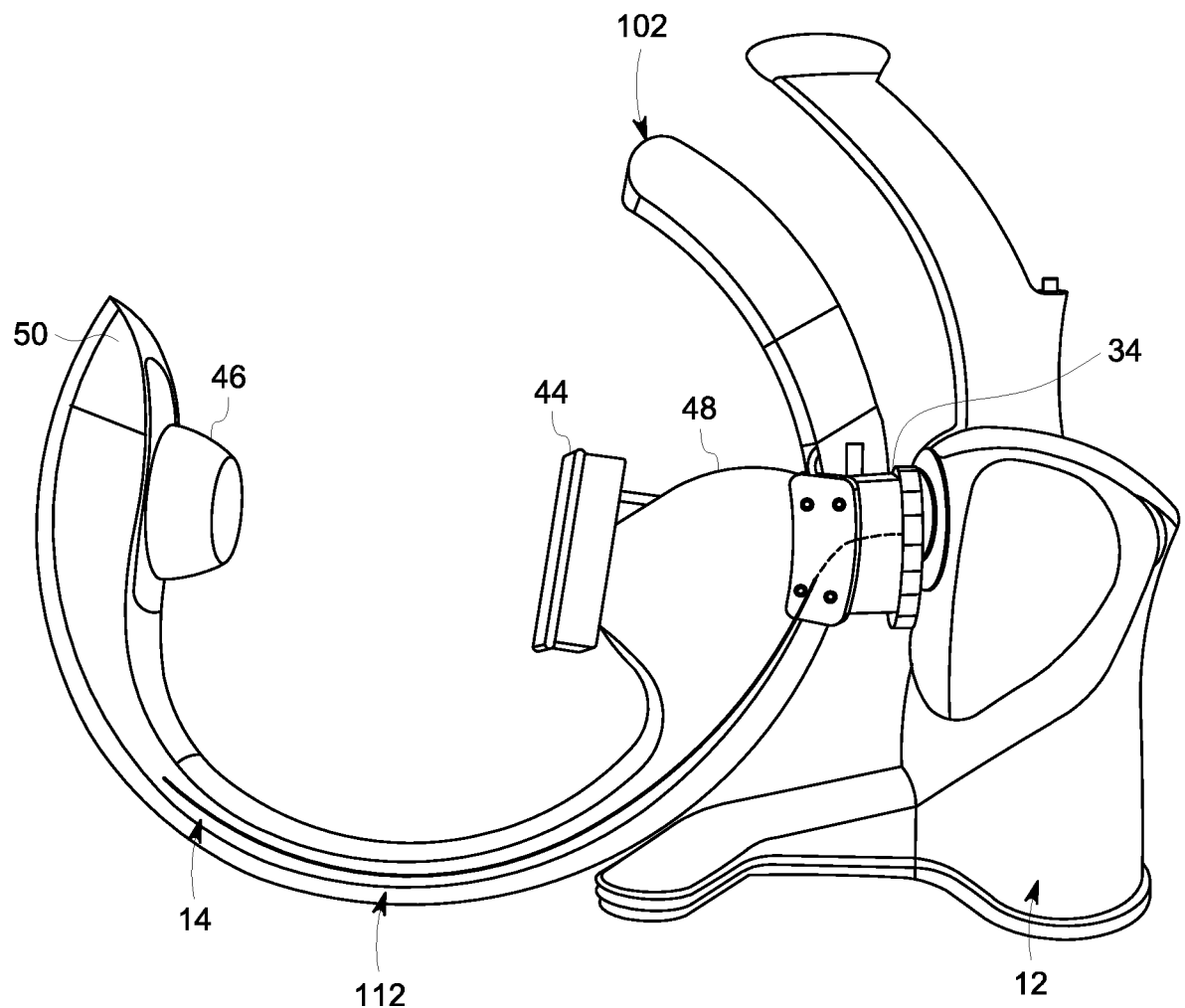
FIG. 8 is a partially broken away, side elevational view of the C-arm imaging system of FIG. 6 with the detector rotated −105 degrees relative to the position of FIG. 6.

Referring now to FIGS. 6-8, the cable management system 100 can include a housing 102 formed with only an upper housing 130, with a corresponding change in the orientation of the cable chain 112 into an upwardly extending loop 140 located in the interior 110 of the housing 102. In this configuration, the first end 126 of the cable chain 112 is disposed within the interior 110 of the housing 102 but is located adjacent the carriage 34. From the end 126, the cable chain 112 extends upwardly from the carriage 34 along the housing 102 and inverts, i.e., curves inwardly and downwardly towards the C-arm 14, at the end 108 of the housing 102 opposite the carriage 34 when the C-arm 14 is disposed in a vertical position, as shown in FIG. 6. The cable chain 112 extends from the inversion within the housing 102 adjacent and along the outer surface 138 of the C-arm 14 within the space 125 to the connection point 128 where the opposite, second end 129 of the cable chain 112 is affixed to the C-arm 14, as discussed previously. However, in this embodiment, the connection point 128 is located on the C-arm 14 approximately equidistant from the detector 44 and the X-ray source 46 in order to accommodate the desired length of the cable chain 112. In this position of the C-arm 14, the entire cable chain 112 is covered by the housing 102 and allows for spinning of the C-arm 14 along the axis 32 without interference from the cable chain 112.

In this configuration, of the cable management system 100, when the C-arm 14 moves to the position shown in FIG. 7 with the detector 44 spaced from the base 12, the inversion of the cable chain 112 is moved out of the housing 102 as a result of movement of the C-arm 14 to be disposed above the C-arm 14. However, due to the position of the connection point 128, as well as any inclusion of the groove 136 and/or engagement members 134 on the outer surface 138 of the C-arm 14, the cable chain 112 can be readily retained in this position with creating obstructions in the area surrounding the C-arm 14.

Conversely, when the C-arm 14 is moved to the position of FIG. 8, the inversion of cable chain 112 is moved along the housing 102 to adjacent the carriage 34, with the remainder of the cable chain 112 extending along the C-arm 14 to the connection point 128. IN this position the provision of the groove 136 and/or the engagement members 134 on the outer surface of the C-arm 14 assist to hold the cable chain 112 in alignment with and/or within the profile of the C-arm 14 to prevent the formation of any obstructions in the area surrounding the C-arm 14 by the cable chain 112.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A C-arm x-ray imaging device comprising:
   a base;
   a carriage operably connected to the base and having at least one axis of movement with respect to the base
   a C-arm movably connected to the carriage, the C-arm including an x-ray source and an x-ray detector disposed thereon in alignment with one another; and
   a cable management system comprising:
      a housing disposed on the carriage, the housing defining an interior;
      a number of cables extending from the base into the interior of the housing;
      a cable chain having a first end secured within the interior of the housing and a second end affixed to the C-arm, the cable chain defining a channel therein that receives the number of cables to direct the number of cables from the base to the C-arm,
   wherein the C-arm includes a groove extending along an outer surface of the C-arm capable of receiving a portion of the cable chain therein,
   wherein the C-arm includes a number of engagement members disposed within the groove and releasably engageable with the cable chain, and
   wherein the number of engagement members are selected from a cam operated holding member, or a flexible or spring-biased holding member, or combinations thereof.

2. The C-arm x-ray imaging device of claim 1, wherein the housing includes a number of engagement members disposed within the interior of the housing and releasably engageable with the cable chain.

3. The C-arm x-ray imaging device of claim 1, wherein the first end of the cable chain is secured to the housing opposite the carriage.

4. The C-arm x-ray imaging device of claim 1, wherein the first end of the cable chain is secured to the housing adjacent the carriage.

5. The C-arm x-ray imaging device of claim 1, wherein the housing includes an upper portion extending upwardly from the carriage and a lower portion extending downwardly from the carriage.

6. The C-arm x-ray imaging device of claim 1, wherein the cable management system retains the number of cables in alignment with the C-arm in any orientation of the C-arm relative to the base.

7. The C-arm x-ray imaging device of claim 1, wherein the cable management system retains the number of cables within a profile of the housing and the C-arm in any orientation of the C-arm relative to the base.

8. A cable management system for a C-arm X-ray imaging device, the cable management system comprising:
   a housing adapted to be secured on a rotating component of a base for the imaging device, the housing defining an interior;
   a number of cables adapted to be connected between the base for the imaging system and a C-arm;
   a cable chain having a first end secured within the interior of the housing and a second end adapted to be secured to the C-arm, the cable chain defining a channel therein that receives the number of cables to direct the number of cables from the base to the C-arm,
   wherein the cable management system is configured to retain the number of cables in alignment with the C-arm in any orientation of the C-arm relative to the base, the C-arm including a groove formed in an outer surface of the C-arm and in which the cable chain is at least partially disposed, and a number of engagement members disposed within the groove and releasably engageable with the cable chain,
   wherein the number of engagement members are selected from a cam operated holding member, or a flexible or spring-biased holding member, or combinations thereof.

9. The cable management system of claim 8, further comprising a number of engagement members disposed within the interior of the housing and releasably engageable with the cable chain.

10. The cable management system of claim 8, wherein cable chain curves upwardly within the housing.

11. The cable management system of claim 8, wherein cable chain curves downwardly within the housing.

12. The cable management system of claim 8, wherein the groove has dimensions that enable the groove to receive the cable chain entirely within a profile of the C-arm.

13. A method of managing the position of cables connecting a detector and an x-ray source of a C-arm to a base of a C-arm x-ray imaging device, the method comprising the steps of:
   providing a C-arm x-ray imaging device comprising:
      a base;
      a carriage operably connected to the base and having at least one axis of movement with respect to the base;
      a C-arm movably connected to the carriage, the C-arm including an x-ray source and an x-ray detector disposed thereon in alignment with one another; and
      a cable management system comprising:
         a housing disposed on the carriage, the housing defining an interior;
         a number of cables extending from the base into the interior of the housing;
         a cable chain having a first end secured within the interior of the housing and a second end affixed to the C-arm, the cable chain defining a channel therein that receives the number of cables to direct the number of cables from the base to the C-arm;
   placing the number of cables within the cable chain; and
   moving the C-arm relative to the carriage; and
   maintaining the cable chain within a profile of at least one of the housing or the C-arm,
   wherein the C-arm includes a groove formed in an outer surface of the C-arm,
   wherein the step of maintaining the cable chain within the profile of at least one of the housing or the C-arm comprises positioning the cable chain within the groove,
   wherein the step of positioning the cable chain within the groove comprises engaging the cable chain with a number of releasable engagement members disposed within the groove, and
   wherein the number of releasable engagement members are selected from a cam operated holding member, or a flexible or spring-biased holding member, or combinations thereof.

14. The method of 13, wherein the step of maintaining the cable chain within the profile of at least one of the housing or the C-arm, comprises engaging the cable chain with a number releasable engagement members within the housing.

\* \* \* \* \*